US012697169B2

(12) United States Patent (10) Patent No.: US 12,697,169 B2

Curran (45) Date of Patent: Aug. 4, 2026

(54) SYSTEMS AND METHODS FOR MONITORING RETURN PATCH IMPEDANCES

(71) Applicant: St. Jude Medical, Cardiology Division, Inc., St. Paul, MN (US)

(72) Inventor: Timothy G. Curran, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 840 days.

(21) Appl. No.: 17/926,427

(22) PCT Filed: May 6, 2021

(86) PCT No.: PCT/US2021/031081

§ 371 (c)(1),
(2) Date: Nov. 18, 2022

(87) PCT Pub. No.: WO2021/236341

PCT Pub. Date: Nov. 25, 2021

(65) Prior Publication Data

US 2023/0190364 A1 Jun. 22, 2023

Related U.S. Application Data

(60) Provisional application No. 63/027,660, filed on May 20, 2020.

(51) Int. Cl.
| | |
|---|---|
| *A61B 18/14* | (2006.01) |
| *A61B 18/12* | (2006.01) |
| *A61B 18/16* | (2006.01) |
| *A61B 18/00* | (2006.01) |

(52) U.S. Cl.
CPC ...... *A61B 18/1492* (2013.01); *A61B 18/1206* (2013.01); *A61B 18/16* (2013.01);
(Continued)

(58) Field of Classification Search
CPC . A61B 18/00; A61B 18/1206; A61B 18/1492; A61B 18/16; A61B 2018/00351;
(Continued)

(56) References Cited

U.S. PATENT DOCUMENTS

| | | | | |
|---|---|---|---|---|
| 4,303,073 A | 12/1981 | Archibald | | |
| 4,848,335 A | * 7/1989 | Manes | .................. | A61B 18/16 |
| | | | | 128/908 |

(Continued)

OTHER PUBLICATIONS

Hogenauer, Eugene B., "An economical class of digital filters for decimation and interpolation", IEEE Transactions on Acoustics, Speech, and Signal Processing, ASSP-29, No. 2, Apr. 1981, DOI:10. 1109/TASSP.1981.1163535.
(Continued)

*Primary Examiner* — Khadijeh A Vahdat
(74) *Attorney, Agent, or Firm* — DENTONS Durham Jones Pinegar

(57) ABSTRACT

Systems and methods for monitoring return patch impedances are provided. A tissue therapy system includes a catheter comprising at least one electrode, the catheter implantable in a patient, a first return patch electrode configured to be applied to skin of the patient, a second return patch electrode configured to be applied to the skin of the patient, and an impedance measuring circuit lectrically coupled to the at least one catheter electrode, the first return patch electrode, and the second return patch electrode. The impedance measuring circuit is configured to drive currents between the at least one catheter electrode, the first return patch electrode, and the second return patch electrode, detect, using a voltage at the at least one catheter electrode as a reference voltage, voltages generated in response to the driven currents, and measure impedances based on the driven currents and the detected voltages.

19 Claims, 5 Drawing Sheets

(52) U.S. Cl.
     CPC .............. *A61B 2018/00351* (2013.01); *A61B
          2018/00577* (2013.01); *A61B 2018/00613*
          (2013.01); *A61B 2018/0072* (2013.01); *A61B
          2018/00875* (2013.01); *A61B 2018/00892*
          (2013.01); *A61B 2018/00898* (2013.01); *A61B
          2018/128* (2013.01); *A61B 2018/167* (2013.01)

(58) Field of Classification Search
     CPC ........... A61B 2018/00357; A61B 2018/00375;
          A61B 2018/00577; A61B 2018/00613;
          A61B 2018/0072; A61B 2018/00839;
          A61B 2018/00875; A61B 2018/00892;
          A61B 2018/00898; A61B 2018/128;
          A61B 2018/167
     See application file for complete search history.

(56)                References Cited

U.S. PATENT DOCUMENTS

| 6,007,532 | A | 12/1999 | Netherly |
| 6,063,075 | A | 5/2000 | Mihori |
| 7,263,397 | B2 | 8/2007 | Hauck |
| 7,938,825 | B2 | 5/2011 | Sturm |
| 8,790,337 | B2 | 7/2014 | Behnke |
| 2007/0073284 | A1 | 3/2007 | Sturm |
| 2008/0071263 | A1 | 3/2008 | Blaha |
| 2009/0171345 | A1 | 7/2009 | Miller |
| 2016/0242667 | A1 | 8/2016 | Fay |
| 2019/0117113 | A1 | 4/2019 | Curran |
| 2019/0183378 | A1 | 6/2019 | Mosesov |
| 2019/0307500 | A1 | 10/2019 | Byrd |

OTHER PUBLICATIONS

International Search Report and Written Opinion issued in International Patent Application No. PCT/US2021/031081, mailed Sep. 1, 2021, 16 pages.

* cited by examiner

SYSTEMS AND METHODS FOR MONITORING RETURN PATCH IMPEDANCES

CROSS-REFERENCE TO RELATED APPLICATIONS

This application claims priority to international application No. PCT/US2021/031081. filed May 6, 2021, which claims priority to U.S. provisional application Ser. No. 63/027,660, filed May 20, 2020, both of which are incorporated herein by reference in their entirety.

FIELD OF THE DISCLOSURE

The present disclosure relates generally to tissue therapy systems. In particular, the present disclosure relates to measuring impedances associated with return patch electrodes in tissue therapy systems.

BACKGROUND

It is generally known that ablation therapy may be used to treat various conditions afflicting the human anatomy. One such condition in which ablation therapy finds a particular application in, for example, is the treatment of atrial arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter).

Arrhythmia (i.e., irregular heart rhythm) can create a variety of dangerous conditions including loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

Electroporation is a non-thermal ablation technique that involves applying strong electric-fields that induce pore formation in the cellular membrane. Electroporation therapy involves electric-field induced pore formation on the cellular membrane. The electric field may be induced by applying a relatively short duration pulse which may last, for instance, from a nanosecond to several milliseconds. Such a pulse may be repeated to form a pulse train. When such an electric field is applied to tissue in an in vivo setting, the cells in the tissue are subjected to trans-membrane potential, which opens the pores on the cell wall. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation.

Irreversible electroporation treats irregular heart rhythms by isolating electrical pathways within the heart. In at least some irreversible electroporation systems, a surface body patch receives return current from a multi-electrode catheter positioned in the heart. However, in such systems, it may be difficult to determine whether the patch is properly attached to the patient, and whether a reasonable impedance exists between the catheter and the patch.

BRIEF SUMMARY OF THE DISCLOSURE

In one embodiment, the present disclosure is directed to a tissue therapy system. The tissue therapy system includes a catheter comprising at least one electrode, the catheter implantable in a patient, a first return patch electrode configured to be applied to skin of the patient, a second return patch electrode configured to be applied to the skin of the patient, and an impedance measuring circuit electrically coupled to the at least one catheter electrode, the first return patch electrode, and the second return patch electrode. The impedance measuring circuit is configured to drive currents between the at least one catheter electrode, the first return patch electrode, and the second return patch electrode, detect, using a voltage at the at least one catheter electrode as a reference voltage, voltages generated in response to the driven currents, and measure impedances based on the driven currents and the detected voltages.

In another embodiment, the present disclosure is directed to an impedance measuring circuit for use in a tissue therapy system, the impedance measuring circuit electrically coupleable between i) at least one electrode of a catheter implantable in a patient, ii) a first return patch electrode configured to be applied to skin of the patient, and iii) a second return patch electrode configured to be applied to the skin of the patient. The impedance measuring circuit is configured to drive currents between the at least one catheter electrode, the first return patch electrode, and the second return patch electrode, detect, using a voltage at the at least one catheter electrode as a reference voltage, voltages generated in response to the driven currents, and measure impedances based on the driven currents and the detected voltages.

In yet another embodiment, the present disclosure is directed to a method of measuring impedances in a tissue therapy system. The method includes driving, using an impedance measuring circuit, currents between i) at least one electrode of a catheter implanted in a patient, ii) a first return patch electrode applied to skin of the patient, and iii) a second return patch electrode applied to the skin of the patient, detecting, by the impedance measuring circuit, using a voltage at the at least one catheter electrode as a reference voltage, voltages generated in response to the driven currents, and measuring impedances based on the driven currents and the detected voltages.

The foregoing and other aspects, features, details, utilities and advantages of the present disclosure will be apparent from reading the following description and claims, and from reviewing the accompanying drawings.

DETAILED DESCRIPTION OF THE DISCLOSURE

The present disclosure provides systems and methods for monitoring return patch impedances. A tissue therapy system includes a catheter comprising at least one electrode, the catheter implantable in a patient, a first return patch electrode configured to be applied to skin of the patient, a second return patch electrode configured to be applied to the skin of the patient, and an impedance measuring circuit electrically coupled to the at least one catheter electrode, the first return patch electrode, and the second return patch electrode. The impedance measuring circuit is configured to drive currents between the at least one catheter electrode, the first return patch electrode, and the second return patch electrode, detect, using a voltage at the at least one catheter electrode as a reference voltage, voltages generated in response to the driven currents, and measure impedances based on the driven currents and the detected voltages.

Although the embodiments detailed herein are discussed in the context of irreversible electroporation systems, those of skill in the art will appreciate that the systems and methods described herein may also be used in radio frequency (RF) ablation systems, neuromodulation systems, etc. RF ablation systems provide similar therapy to irreversible electroporation systems, but heat tissue using RF energy.

Figure 1A:
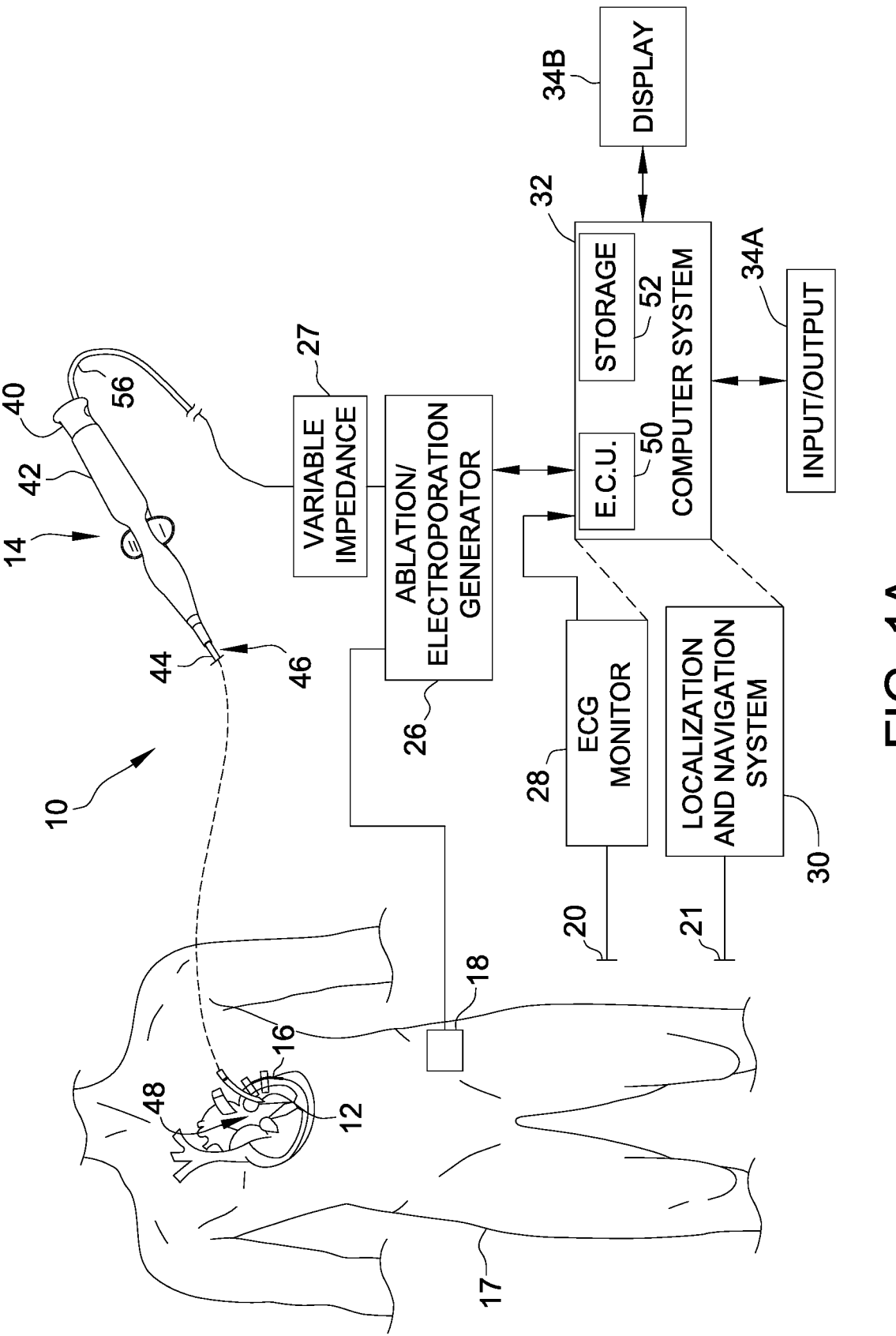
FIG. 1A is a schematic and block diagram view of a system for electroporation therapy.

FIG. 1A is a block diagram view of a system 10 for electroporation therapy. In general, system 10 includes a catheter electrode assembly 12 disposed at a distal end 48 of a catheter 14. As used herein, "proximal" refers to a direction toward the end of the catheter near the clinician and "distal" refers to a direction away from the clinician and (generally) inside the body of a patient. The electrode assembly includes one or more individual, electrically-isolated electrode elements. Each electrode element, also referred to herein as a catheter electrode, is individually wired such that it can be selectively paired or combined with any other electrode element to act as a bipolar or a multipolar electrode.

System 10 may be used for irreversible electroporation (IRE) to destroy tissue. In particular, system 10 may be used for electroporation-induced primary necrosis therapy, which refers to the effects of delivering electrical current in such a manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration pulses (e.g., having a 0.1 to 20 millisecond (ms) duration) between closely spaced electrodes capable of delivering an electric field strength of about 0.1 to 1.0 kilovolts/centimeter (kV/cm). System 10 may be used, for example, with a high output hoop catheter (See FIGS. 1B and 1C) for high output (e.g., high voltage and/or high current) electroporation procedures.

In one embodiment, all electrodes of the hoop catheter deliver an electric current simultaneously. That is, the electrodes are electrically connected in parallel during the application. Delivering electric current simultaneously using a plurality of electrodes arranged in a circular fashion facilitates creating a sufficiently deep lesion for electroporation. To facilitate activating electrodes simultaneously, the electrodes may be switchable between being connected to a 3D mapping system and being connected to EP amplifiers.

When using a circular hoop catheter, the current density in surrounding tissue decays linearly with distance from the electrodes when all electrodes deliver an electric current simultaneously. If, however, less than all the electrodes delivery an electric current simultaneously, the current density near electrodes that do not participate in current delivery will decay exponentially, instead of linearly. The exponential decay in current may result in insufficient lesion depth, gaps in an ablation line, and undesired procedural outcomes. Accordingly, in at least some of the embodiments, current is delivered simultaneously by all electrodes (e.g., even those with low or no tissue contact). Simultaneous delivery of all electrodes in a circular arrangement may also be used for other types of electrical energy. For example, for RF ablation, simultaneous delivery (i.e., with an in-phase electrical RF current) via all electrodes (instead of a phased array or sequential delivery) may result in improved outcomes.

For a hoop catheter, when the hoop diameter is minimized, multiple electrodes will overlap, such that a subset of the electrodes forms a circle by themselves. Accordingly, in such a configuration, current can be simultaneously delivered using the subset of the electrodes without using the remaining electrodes, as the remaining electrodes overlap the subset of electrodes. In such an embodiment, determining which electrodes to use may be accomplished by determining which electrodes have the best tissue contact. By using less than all electrodes, the total energy delivered by the hoop catheter is reduced.

Irreversible electroporation through a multielectrode hoop catheter may enable pulmonary vein isolation in as few as one shock per vein, which may produce much shorter procedure times compared to sequentially positioning a radiofrequency (RF) ablation tip around a vein.

It should be understood that while the energization strategies are described as involving DC pulses, embodiments may use variations and remain within the spirit and scope of the disclosure. For example, exponentially-decaying pulses, exponentially-increasing pulses, and combinations may be used.

Further, it should be understood that the mechanism of cell destruction in electroporation is not primarily due to heating effects, but rather to cell membrane disruption through application of a high-voltage electric field. Thus, electroporation may avoid some possible thermal effects that may occur when using radio frequency (RF) energy. This "cold therapy" thus has desirable characteristics.

With this background, and now referring again to FIG. 1A, system 10 includes a catheter electrode assembly 12 including at least one catheter electrode. Electrode assembly 12 is incorporated as part of a medical device such as a catheter 14 for electroporation therapy of tissue 16 in a body 17 of a patient. In the illustrative embodiment, tissue 16 includes heart or cardiac tissue. It should be understood, however, that embodiments may be used to conduct electroporation therapy with respect to a variety of other body tissues.

FIG. 1A further shows a plurality of return electrodes designated 18, 20, and 21, which are diagrammatic of the body connections that may be used by the various subsystems included in overall system 10, such as an electroporation generator 26, an electrophysiology (EP) monitor such as an ECG monitor 28, and a localization and navigation system 30 for visualization, mapping, and navigation of internal body structures. In the illustrated embodiment, return electrodes 18, 20, and 21 are patch electrodes. It should be understood that the illustration of a single patch electrode is diagrammatic only (for clarity) and that such sub-systems to which these patch electrodes are connected may, and typically will, include more than one patch (body surface) electrode, and may include split patch electrodes (as described herein). In other embodiments, return electrodes 18, 20, and 21 may be any other type of electrode suitable for use as a return electrode including, for example, one or more catheter electrodes. Return electrodes that are catheter electrode may be part of electrode assembly 12 or part of a separate catheter (not shown). System 10 may further include a main computer system 32 (including an electronic control unit 50 and data storage-memory 52), which may be integrated with localization and navigation system 30 in certain embodiments. System 32 may further include conventional interface components, such as various user input/ output mechanisms 34a and a display 34b, among other components.

Electroporation generator 26 is configured to energize the electrode element(s) in accordance with an electroporation energization strategy, which may be predetermined or may be user-selectable. For electroporation-induced primary necrosis therapy, generator 26 may be configured to produce an electric current that is delivered via electrode assembly 12 as a pulsed electric field in the form of short-duration DC pulses (e.g., a nanosecond to several milliseconds duration, 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude must be increased to achieve electroporation.

Electroporation generator 26, sometimes also referred to herein as a DC energy source, is a monophasic electroporation generator 26 configured to generate a series of DC energy pulses that all produce current in the same direction. In other embodiments, electroporation generator is biphasic or polyphasic electroporation generator configured to produce DC energy pulses that do not all produce current in the same direction. In some embodiments, electroporation generator 26 is configured to output energy in DC pulses at selectable energy levels, such as fifty joules, one hundred joules, two hundred joules, and the like. Other embodiments may have more or fewer energy settings and the values of the available setting may be the same or different. For successful electroporation, some embodiments utilize the two hundred joule output level. For example, electroporation generator 26 may output a DC pulse having a peak magnitude of about between about negative one kV and about negative two kV at the two hundred joule output level. In some embodiments, electroporation generator 26 outputs a DC pulse having a peak magnitude of about between about negative 1.5 kV and about negative 2.0 kV. Other embodiments may output any other suitable voltage, including a positive voltage.

In some embodiments, a variable impedance 27 allows the impedance of system 10 to be varied to limit arcing from the catheter electrode of catheter 14. Moreover, variable impedance 27 may be used to change one or more characteristics, such as amplitude, duration, pulse shape, and the like, of an output of electroporation generator 26. Although illustrated as a separate component, variable impedance 27 may be incorporated in catheter 14 or generator 26.

With continued reference to FIG. 1A, as noted above, catheter 14 may include functionality for electroporation and in certain embodiments also an ablation function (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal 48 end. Catheter 14 may also include other conventional components not illustrated herein such as a temperature sensor, additional electrodes, and corresponding conductors or leads. Connector 40 provides mechanical and electrical connection(s) for cable 56 extending from generator 26. Connector 40 may include conventional components known in the art and as shown is disposed at the proximal end of catheter 14.

Handle 42 provides a location for the clinician to hold catheter 14 and may further provide means for steering or the guiding shaft 44 within body 17. For example, handle 42 may include means to change the length of a guidewire extending through catheter 14 to distal end 48 of shaft 44 or means to steer shaft 44. Moreover, in some embodiments, handle 42 may be configured to vary the shape, size, and/or orientation of a portion of the catheter. Handle 42 is also conventional in the art and it will be understood that the construction of handle 42 may vary. In an alternate embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14. Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced/retracted and/or steered or guided through body 17 to a desired location such as the site of tissue 16, including through the use of guidewires or other means known in the art.

In some embodiments, catheter 14 is a hoop catheter having catheter electrodes (not shown) distributed about one or more hoops at the distal end of shaft 44. The diameter of the hoop(s) may be variable. In some embodiments, the hoop catheter has a maximum diameter of about twenty-seven millimeters (mm). In some embodiments, the hoop diameter is variable between about fifteen mm and about twenty eight mm. Alternatively, the catheter may be a fixed diameter hoop catheter or may be variable between different diameters. In some embodiments, catheter 14 has fourteen catheter electrodes. In other embodiments, catheter 14 includes ten catheter electrodes, twenty catheter electrodes, or any other suitable number of electrodes for performing electroporation. In some embodiments, the catheter electrodes are ring electrodes, such as platinum ring electrodes. Alternatively, the catheter electrodes may be any other suitable type of electrodes, such as single sided electrode or electrodes printed on a flex material. In various embodiments, the catheter electrodes have lengths of 1.0 mm, 2.0 mm, 2.5 mm, and/or any other suitable length for electroporation.

Localization and navigation system 30 may be provided for visualization, mapping and navigation of internal body structures. Localization and navigation system 30 may include conventional apparatus known generally in the art (e.g., an EnSite Precision™ System, commercially available from Abbott Laboratories. and as generally shown with reference to commonly assigned U.S. Pat. No. 7,263,397 titled "Method and Apparatus for Catheter Navigation and Location and Mapping in the Heart," the entire disclosure of which is incorporated herein by reference). It should be understood, however, that this system is an example only, and is not limiting in nature. Other technologies for locating/navigating a catheter in space (and for visualization) are known, including for example, the CARTO navigation and location system of Biosense Webster, Inc., the Rhythmia® system of Boston Scientific Schimed, Inc., the KODEX® system of Koninklijke Philips N.V., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system.

Figure 1B:
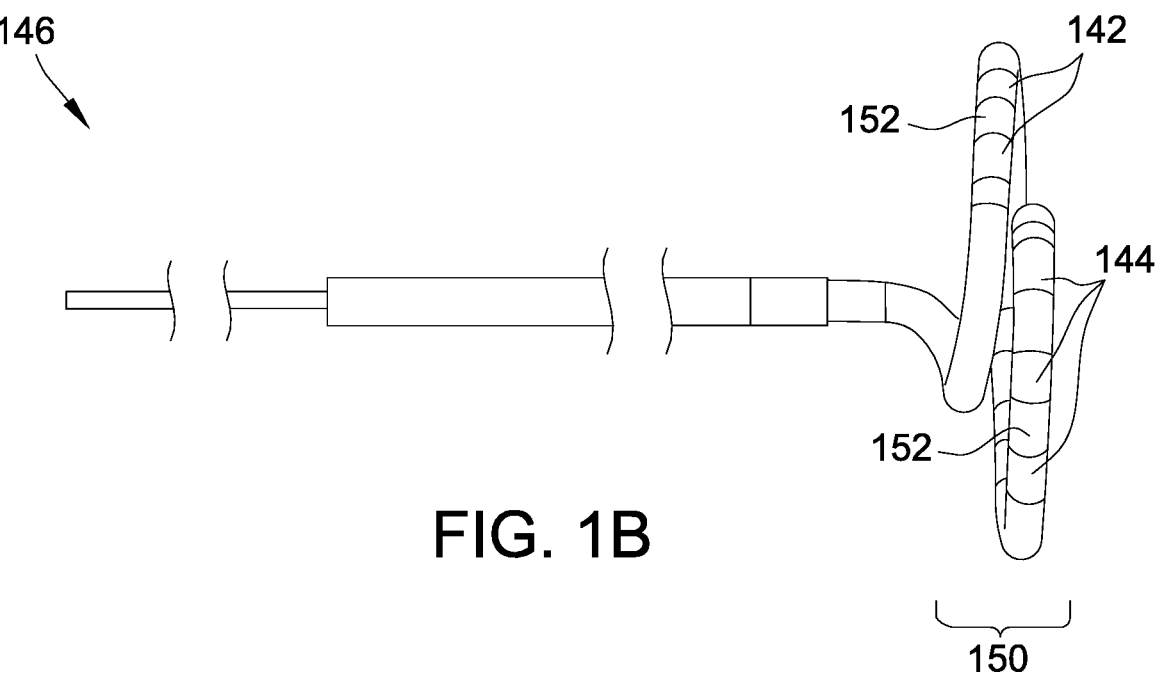
FIGS. 1B and 1C are views of one embodiment of a distal hoop subassembly that may be used with the catheter shown in FIG. 1A.
Figure 1C:
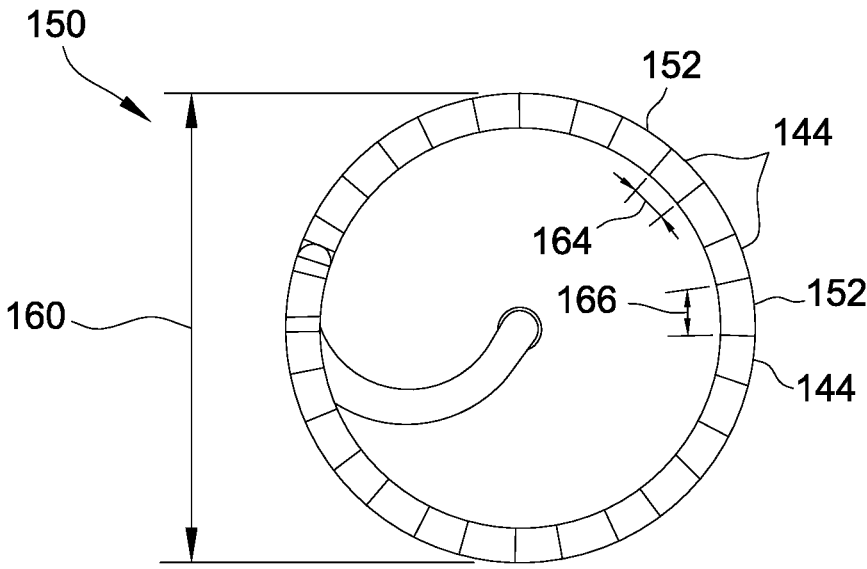

FIGS. 1B and 1C are views of one embodiment of a distal hoop subassembly 146 that may be used with catheter 14 in system 10. Those of skill in the art will appreciate that, in other embodiments, any suitable catheter may be used. Specifically, FIG. 1B is a side view of distal hoop subassembly 146 with a variable diameter hoop 150 at a distal end 142. FIG. 1C is a top view of variable diameter hoop 150 of distal hoop subassembly 146.

Variable diameter hoop 150 is variable between an expanded (also referred to as "open") diameter 160 (shown in FIG. 1C) and a retracted (also referred to as "closed") diameter 160 (not shown). In the example embodiment, an expanded diameter 160 is twenty seven mm and a retracted diameter 160 is fifteen mm. In other embodiments, diameter 160 may be variable between any suitable open and closed diameters 160.

Variable diameter hoop 150 includes fourteen catheter electrodes 144 evenly spaced around the circumference of variable diameter hoop 150. Catheter electrodes 144 are platinum ring electrodes configured to conduct and/or discharge electrical current in the range of one thousand volts and/or ten amperes. In other embodiments, variable diameter hoop 150 may include any suitable number of catheter electrodes 144 made of any suitable material. Catheter electrodes 144 may include any catheter electrode suitable to conduct high voltage and/or high current (e.g., in the range of one thousand volts and/or ten amperes). Each catheter electrode 144 is separated from each other catheter electrode by an insulated gap 152. In the example embodiment, each catheter electrode 144 has a same length 164 (shown in FIG. 1C) and each insulated gap 152 has a same length 166 as each other gap 152. Length 164 and length 166 are both about 2.5 mm in the example embodiment. In other embodiments, length 164 and length 166 may be different from each other. Moreover, in some embodiments, catheter electrodes 144 may not all have the same length 164 and/or insulated gaps 152 may not all have the same length 166. In some embodiments, catheter electrodes 144 are not spaced evenly around the circumference of variable diameter hoop 150.

Diameter 160 and catheter electrode 144 spacing may be developed to provide a targeted range of energy density to tissue, as well as to provide sufficient electroporation coverage for different human anatomic geometries. In general, a sufficient number of electrodes 144 with appropriate lengths 164 are desired to provide substantially even and continuous coverage around the circumference of variable diameter hoop 150, while still allowing enough flexibility to allow variable diameter hoop 150 to expand and contract to vary diameter 160 to the desired extremes. As mentioned above, length 164 of catheter electrodes 144 may be varied. Increasing length 164 of catheter electrodes 144 may increase coverage of electrodes 144 around the circumference of hoop 150 while also decreasing current density (by increasing the surface area) on electrodes 144, which may help prevent arcing during electroporation operations. Increasing length 164 too much, however, may prevent variable diameter hoop 150 from forming a smooth circular shape and may limit the closed diameter 160 of variable diameter hoop 150. Additionally, too great a length 164 may increase the surface area of catheter electrodes 144 to a point that the current density applied to catheter electrodes 144 by a power source is below the minimum current density needed for successful therapy. Conversely, decreasing length 164 decreases the surface area, thereby increasing the current density (assuming no other system changes) on catheter electrodes 144. As discussed above, greater current densities may lead to increased risk of arcing during electroporation, and may result in larger additional system resistances needing to be added to prevent electroporation. Moreover, in order to get a desired, even coverage about the circumference of variable diameter hoop 150, more catheter electrodes 144 may be needed if length 164 is decreased. Increasing the number of catheter electrodes 144 on variable diameter hoop 150 may prevent variable diameter hoop 150 from being able to be contracted to a desired minimum diameter 160.

To monitor operation of system 10, the impedance between electrodes in electrode assembly 12 and a return patch (e.g., return electrode 18) on the surface of body 17 can be measured prior to delivery of therapy (i.e., prior to applying energy pulses). This may be accomplished by delivering a relatively low energy irreversible electroporation pulse, and determining how much current and/or energy was delivered to the patient. However, even low energy irreversible electroporation pulses may cause discomfort to the patient. Accordingly, it would be desirable to determine impedances between the electrodes in electrode assembly 12 and a return patch using alternative techniques.

Additionally, and in some embodiments, the system is configured to determine when the return patch is properly adhered to body 17, for both safety and efficacy purposes. A poorly connected patch may result in relatively high current levels through a small area, which is undesirable. Further, a poorly connected patch may negatively impact therapy delivery, as higher currents may be required to overcome higher than expected patch impedances.

The systems and methods described herein enable measuring impedances between catheter electrodes and one or more return patches, and also enable determining whether the one or more return patches are properly applied. This is accomplished using an impedance measuring circuit, as described herein. Further, in the embodiments described herein, the impedance measuring circuit is protected from the relatively high voltages of irreversible electroporation pulses such that the impedance measuring circuit may be used continuously without being disconnected and reconnected from and to pulse generation circuitry.

More specifically, the embodiments described herein are capable of simultaneously measuring i) impedances of multiple patch segments of a split patch independently of one another, ii) impedances of multiple return patches independently of one another, and iii) impedances between catheter electrodes and multiple patch segments and/or multiple return patches. Further, the embodiments described herein are capable of tolerating high voltage pulses without requiring disconnection, and are capable of quickly recovering from such pulses.

Figure 2:
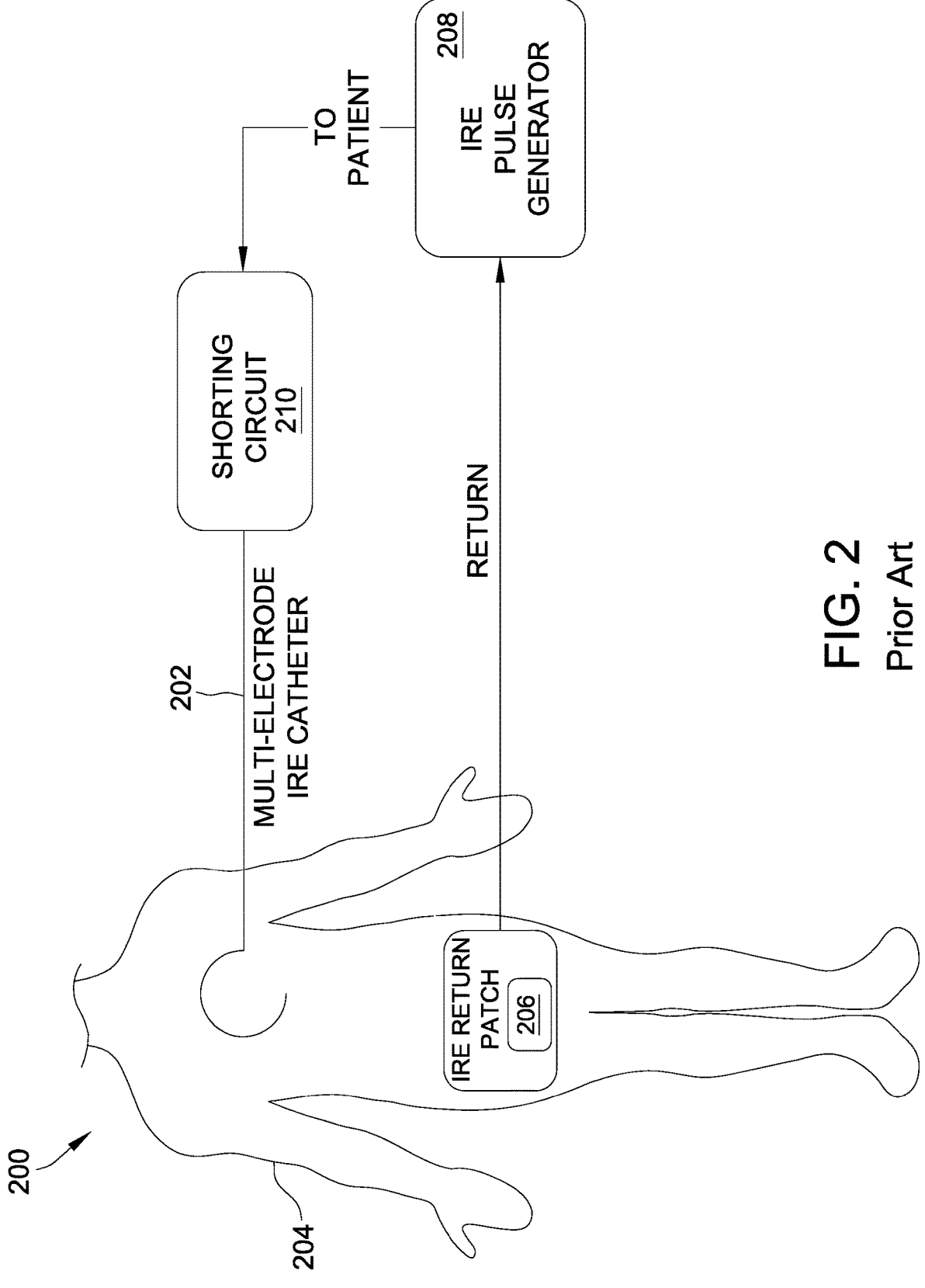
FIG. 2 is a simplified schematic diagram of a known irreversible electroporation (IRE) system.

FIG. 2 is a simplified schematic diagram of a known irreversible electroporation (IRE) system 200. System 200 includes a multi-electrode IRE catheter 202 that is positioned within a patient 204, and an IRE return patch 206 attached to patient 204 (e.g., adhered to the skin of patient 204). System 200 further includes an IRE pulse generator 208.

In this embodiment, system 200 is a monopolar system. Accordingly, during operation, IRE pulse generator 208 generates a monophasic or biphasic pulse, and delivers the pulse to patient 204 via catheter 202. A shorting circuit 210 coupled between pulse generator 208 and catheter 202 ties multiple electrodes of catheter 202 together during delivery of the pulse. Notably, other than shorting circuit 210, an RF ablation system is relatively similar to system 200. Unlike the inventive embodiments described herein, system 200 does not include an impedance measuring circuit.

Figure 3:
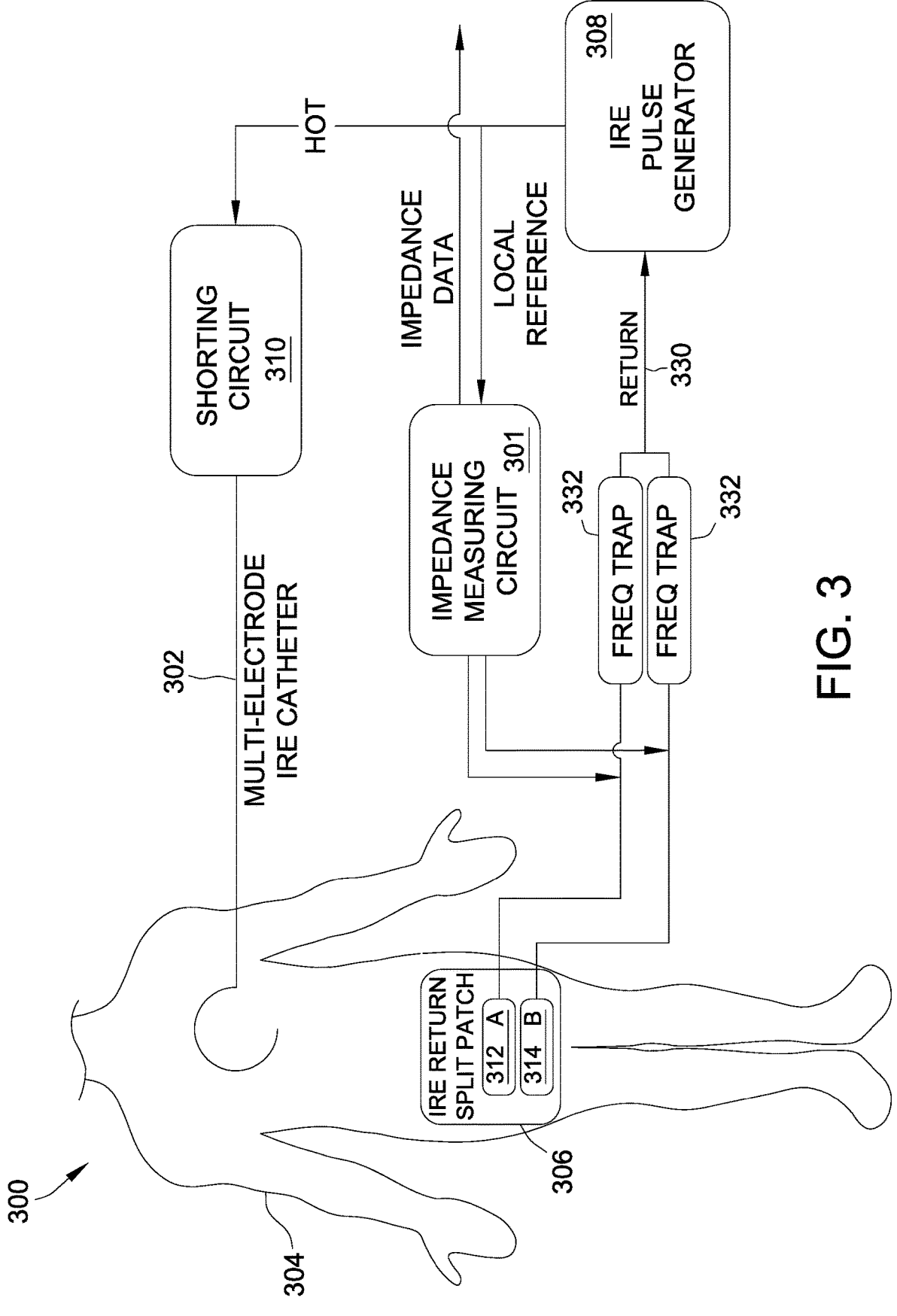
FIG. 3 is a simplified schematic diagram of one embodiment of an IRE system including an impedance measuring circuit.

FIG. 3 is a simplified schematic diagram of one embodiment of an IRE system 300 (broadly, a tissue therapy system) including an impedance measuring circuit 301. Similar to system 200 (shown in FIG. 2), system 300 includes a multi-electrode IRE catheter 302 that is positioned within a patient 304, and an IRE return patch 306 attached to patient 304 (e.g., adhered to the skin of patient 304). System 300 further includes an IRE pulse generator 308, and a shorting circuit 310 coupled between catheter 302 and pulse generator 308.

In this embodiment, return patch 306 is a split electrosurgical pad (also referred to as a split return patch) with a first portion 312 and a second portion 314. First and second portions 312 and 314 may each account for, for example, approximately half of return patch 306. Using a split return patch enables measuring an impedance between first portion 312 and second portion 314 using impedance measuring circuit 301 to facilitate assessing whether return patch 306 is properly adhered to patient 304, as described herein. Impedances between catheter 302 and first and second portions 312 and 314 are also measurable using impedance measuring circuit 301, as described herein.

Those of skill in the art will appreciate that impedance measuring circuit 301 may also be used to measure impedances from catheter 302 to a non-split patch, to measure impedances from catheter 302 to multiple different return patches, and/or to measure impedances between multiple different return patches. Further, as described herein, all impedance measurements may be made simultaneously, and impedance measuring circuit 301 is capable of withstanding high-voltage pulses (e.g., IRE pulses generated by pulse generator 308) without being damaged by virtue of high-impedance resistors 340 (shown in FIG. 4).

To measure impedances, relatively small alternating current (AC) currents (e.g., on the order of 2 to 20 microamps RMS) are injected between points of interest. Voltages generated by the currents are then measured and synchronously demodulated as described herein.

Notably, in the systems and methods described herein, catheter 302 (and specifically, electrodes on catheter 302) serves as the reference electrode when measuring impedances. In contrast, in at least some known systems, catheter electrodes are considered electrically 'hot', and the return patch is typically used as the reference electrode.

Here, however, because there are multiple portions of return patch 306 and/or multiple return patches 306, it may be difficult to use one portion of return patch 306 or one return patch 306 (in the case of multiple return patches 306) as the reference electrode. Further, if a return patch 306 or portion of return patch 306 is used as the reference electrode, it is difficult to measure meaningful values if return patch 306 or the portion of return patch 306 is not properly secured to the patient.

In contrast, by using catheter 302 as the reference electrode and treating return patch 306 as electrically 'hot', impedances of first and second portions 312 and 314 may be measured, not just between each other, but also independently of one another to determine whether there is an impedance imbalance between first and second portions 312 and 314. This same concept can be extended to embodiments including multiple return patches 306 (e.g., embodiments used in high power applications at greater than 50 Watts).

To measure multiple different impedances simultaneously, in one embodiment, impedance measuring circuit 301 uses a different frequency for each impedance measurement, as described herein. The frequencies used may share a common base frequency. U.S. Patent Application Publication No. 2019/0117113, filed on Oct. 23, 2018, and U.S. Patent Application Publication No. 2019/0183378, filed on Dec. 19, 2018, both of which are incorporated by reference herein in their entirety, describe additional details regarding simultaneously measuring different impedances using multiple different frequencies.

As noted above, multiple different impedances are measurable using impedance measuring circuit 301. For example, let A represent return patch first portion 312, let B represent return patch second portion 314, and let C represent catheter 302 (assuming electrodes of catheter 302 are shorted together using shorting circuit 310).

In the embodiment shown in FIG. 3, impedance measuring circuit 301 is capable of measuring i) the impedance from first portion 312 to the body of patient 304 (represented as $Z_A$), ii) the impedance from second portion 314 to the body of patient 304 (represented as $Z_B$), iii) the impedance from first portion 312 to catheter 302 (represented as $Z_{AC}$), and iv) the impedance from second portion 314 to catheter 302 (represented as $Z_{BC}$). Notably, in this embodiment, catheter 302 serves as the reference electrode for each impedance measurement.

$Z_A$ and $Z_B$ are an indication of whether return patch 306 is properly adhered to patient 304. Specifically, $Z_A$ and $Z_B$ should have substantially the same value, and their values should fall within a first expected impedance range (e.g., a range of 10 Ohms to 40 Ohms). If however, there is an imbalance between $Z_A$ and $Z_B$ (i.e., $Z_A$ is substantially different than $Z_B$), that imbalance indicates that at least one of first portion 312 and second portion 314 is not properly applied to patient 304.

Accordingly, a processing device (e.g., computer system 50) may compare $Z_A$ and $Z_B$ to one another, and to the first expected impedance range. If $Z_A$ and $Z_B$ are substantially different, and/or if at least one of $Z_A$ and $Z_B$ falls outside the first expected impedance range, system 300 may generate an alert (e.g., an audio and/or visual alert generated using computer system 32) to notify patient 304 and/or the physician. Further, in some embodiments, if $Z_A$ and $Z_B$ are substantially different, and/or if at least one of $Z_A$ and $Z_B$ falls outside the first expected impedance range, system 300 may inhibit pulse generator 308 from supplying an IRE pulse (e.g., providing a protective "lock out" function). If, on the other hand, $Z_A$ and $Z_B$ have substantially similar values and both fall within the first expected impedance range, patient 304 and physician have confidence that return patch 306 is properly adhered prior to delivering an IRE pulse.

$Z_{AC}$ and $Z_{BC}$ provide impedances as seen from catheter 302 to each of first and second portions 312 and 314. The absolute values of each of these impedances may be helpful in determining voltage settings of IRE pulses for desired energy or current delivery. Although each impedance is measured to an associated portion 312, 314 of return patch 306, the overall impedance for each path (with both portions 312 and 314 in parallel) should be relatively similar. This is because most of the impedance along each path occurs at catheter 302, with return patch 306 and patient 304 contributing a relatively small amount. Accordingly, $Z_{AC}$ and $Z_{BC}$ should have substantially the same value, and both values should fall within a second expected impedance range. (e.g., a range of 50 Ohms to 150 Ohms).

Accordingly, a processing device (e.g., computer system 50) may compare $Z_{AC}$ and $Z_{BC}$ to one another, and to the second expected impedance range. If $Z_{AC}$ and $Z_{BC}$ are substantially different, and/or if at least one of $Z_{AC}$ and $Z_{BC}$ falls outside the second expected impedance range, system 300 may generate an alert (e.g., an audio and/or visual alert generated using computer system 32) to notify patient 304 and/or the physician. Further, in some embodiments, if $Z_{AC}$ and $Z_{BC}$ are substantially different, and/or if at least one of $Z_{AC}$ and $Z_{BC}$ falls outside the second expected impedance range, system 300 may inhibit pulse generator 308 from supplying an IRE pulse (e.g., providing a protective "lock out" function). If, on the other hand, $Z_{AC}$ and $Z_{BC}$ have substantially similar values and both fall within the second expected impedance range, patient 304 and physician have confidence that system 300 is properly configured prior to delivering an IRE pulse.

As shown in FIG. 3, impedance measuring circuit 301 is coupled to return patch first portion 312, return patch second portion 314, and catheter 302. Impedance measuring circuit 301 receives local reference values from catheter 302, with catheter serving 302 as the reference electrode for the impedance measurements, as noted above. Impedance measuring circuit 301 outputs impedance data (e.g., to computer system 32) for further processing.

Further, in this embodiment, return patch first portion 312 and return patch second portion 314 are coupled together at a return point 330. Because a single return point 330 is used, frequency traps 332 are coupled between each of first and second portions 312 and 314 and return point 330 to prevent shorting between sensing frequencies carried by first and second portions 312 and 314. Frequency traps 332 are also capable of passing IRE pulses generated by pulse generator 308.

Figure 4:
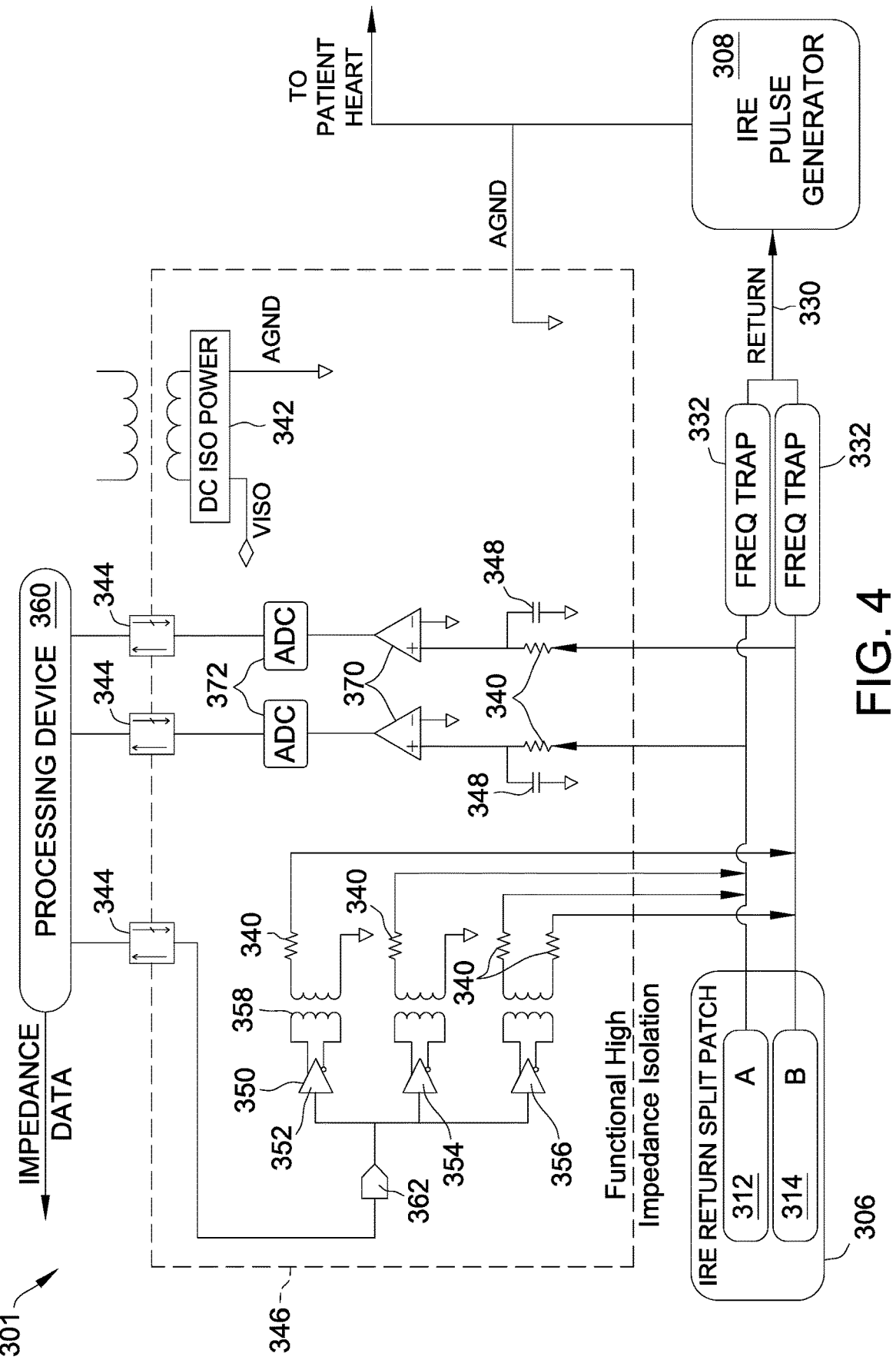
FIG. 4 is a simplified circuit diagram of one embodiment of an impedance measuring circuit that may be used with the system shown in FIG. 3.

FIG. 4 is a simplified circuit diagram of one embodiment of impedance measuring circuit 301 within system 300. Impedance measuring circuit 301 is connected to a reference voltage (indicated as "AGND") from catheter 302 to facilitate measuring impedances as described herein. As shown in FIG. 4, impedance measuring circuit 301 is electrically isolated from other components of system 300. This allows catheter 302 to serve as the reference, with first and second portions 312 and 314 treated as electrically 'hot'. In this embodiment, impedance measuring circuit 301 is electrically isolated using an isolated power source 342 and a plurality of isolators 344 (e.g., optical isolators or capacitive digital couplers) for communicating data across an isolation barrier 346. As will be appreciated by those of skill in the art, impedance measuring circuit 301 may include additional and/or alternative isolation schemes in other embodiments.

High-impedance resistors 340 serve multiple functions, including protecting active circuitry of impedance measuring circuit 301 from IRE pulses. High-impedance resistors 340 may be on the order of 50,000 to 500,000 ohms, and high-impedance resistors 340 need not all have the same value. In some embodiments, multiple high-impedance resistors 340 are electrically coupled together to provide fault tolerance functionality and/or high reliability. It is not necessary to measure impedances during delivery of IRE pulses, but circuit components of impedance measuring circuit 301 should be protected from damage and enabled to recover promptly.

In the case of RF ablation, which may last for many seconds or even minutes, it is possible to measure impedances during active ablation. In such embodiments, high-impedance resistors 340 not only protect input buffers 370, but may also form a low pass RC filter in combination with a capacitor 348. This low pass filter reduces the RF ablation voltage, which may be on the order of 50 to 150 volts RMS, to a safe value to prevent damage and a low enough amplitude such that an input of each input buffer 370 does not saturate. This allows input buffers 370 to continue to measure impedance during active ablation. In this embodiment, the low pass filter has a cutoff frequency which is higher than the measuring frequency but well below typical RF ablation frequencies (e.g., 485 kHz). For example, values of 150 kilo-ohms for high-impedance resistor 340 and 36 pico-farads for capacitor 348 results in a cutoff frequency of approximately 30 kHz.

Impedance measuring circuit 301 includes a plurality of signal generators 350, each signal generator 350 serving as a current source to drive a signal between two points of interest at a predetermined frequency, in order to measure an impedance between the two points of interest. In this embodiment, impedance measuring circuit 301 includes three signal generators 350—a first signal generator 352, a second signal generator 354, and a third signal generator 356. Alternatively, impedance measuring circuit 301 may include additional signal generators 350 (e.g., in embodiments with multiple return patches 306). Each signal generator 350 includes a transformer 358. Transformers 358 and high-impedance resistors 340 provide a simple, independent current source at each predetermined frequency.

In this embodiment, a processing device (e.g., a field-programmable gate array (FPGA)) 360 provides precise frequency excitation to each signal generator 350 by synthesizing sine waves and using a digital-to-analog converter (DAC) 362. Due to high-impedance resistors 340 having a fixed resistance orders of magnitude higher than an impedance of patient 304, and due to an output of DAC 362 having a fixed, predefined amplitude, current levels are essentially constant over a wide range of patient loads.

Currents driven by each signal generator 350 generate voltages that are measured using input buffers 370 (e.g., operational amplifiers). Each input buffer 370 is designed to have an inherently high input impedance (e.g., in the many millions of ohms) and is protected during IRE using at least one high-impedance resistor 340. Input buffers 370 output signals to processing device 360 through associated analog-to-digital converters (ADCs) 372.

To synchronously demodulate signals received from input buffers 370, processing device 360 generates the same frequencies used to drive signal generators 350. Notably, the amplitude of the voltage sensed by input buffers 370 is proportional to the impedance, based on Ohm's law. Specifically, the current driven by signal generator 350 and the measured voltage are known, and the impedance is given by dividing the voltage by the current. Because the current is essentially constant over a wide patient load range, a simple, constant coefficient converts voltage to impedance.

The three frequencies of first, second, and third signal generators 352, 354, and 356 are selected to be independent of one another, and transformers 358 provide independent paths for the generated currents. For each input channel, synchronous demodulation at processing device 360 provides a complex impedance including a real (resistive) element and an imaginary (reactive) element for all three frequencies. Processing device 360 outputs impedance data (e.g., to computer system 32) for further processing. Additional patches may be supported by adding additional signal generators 350 each having unique frequencies.

In this embodiment, first signal generator 352 drives a signal between first portion 312 and second portion 314 to facilitate measuring i) an impedance between first portion 312 and second portion 314, ii) an impedance between first portion 312 and patient 304, and iii) an impedance between second portion 314 and patient. Further, second signal generator 354 drives a signal between first portion 312 and catheter 302 to facilitate measuring an impedance between first portion 312 and catheter 302, and third signal generator 356 drives a signal between second portion 314 and catheter 302 to facilitate measuring an impedance between second portion 314 and catheter 302.

As noted above, frequency traps 332 prevent the sensing frequencies from shorting to each other where first and second portions 312 and 314 join at return point 330. Traps 332 may be implemented, for example, using an inductor in parallel with a capacitor tuned to have a high impedance at the frequencies used. If the three frequencies are relatively close (e.g., separated by 25 Hz each), a single trap 332 in each leg is sufficient. The frequencies may be, for example, in the 16 kHz to 17 kHz range. For example, the three frequencies might be 16500 Hz, 16525 Hz, and 16550 Hz. In other embodiments, any suitable frequency may be used. For example, the frequencies may be as low as 10 kHz and upwards of 50 kHz in some embodiments.

Frequency traps 332 should also be capable of passing IRE pulses (or RF ablation current in RF applications) with relatively low losses. For RF ablation, the capacitor in frequency trap 332 carries the current because the ablation frequency is well above the impedance measuring frequencies used, and the capacitor is sized to carry the current with relatively low losses. In IRE applications, depending on the characteristics of the IRE pulses, current may pass through the capacitor or the inductor. For example, long IRE pulses may be considered direct current (DC), and as such the inductor will pass the current, subject to its inherent DC resistance. In some embodiments, additional clamping components, such as a relatively low voltage transient voltage suppressor (TVS) or a semiconductor protection thyristor may be used in parallel with frequency trap 332, as such devices will conduct when the voltage in either direction exceeds a pre-defined value as specified for the clamping device.

The systems and methods described herein are directed to monitoring return patch impedances. A tissue therapy system includes a catheter comprising at least one electrode, the catheter implantable in a patient, a first return patch electrode configured to be applied to skin of the patient, a second return patch electrode configured to be applied to the skin of the patient, and an impedance measuring circuit electrically coupled to the at least one catheter electrode, the first return patch electrode, and the second return patch electrode. The impedance measuring circuit is configured to drive currents between the at least one catheter electrode, the first return patch electrode, and the second return patch electrode, detect, using a voltage at the at least one catheter electrode as a reference voltage, voltages generated in response to the driven currents, and measure impedances based on the driven currents and the detected voltages.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A tissue therapy system comprising:
a catheter comprising at least one electrode, the catheter insertable in a patient;
a first return patch electrode configured to be applied to skin of the patient;
a second return patch electrode configured to be applied to the skin of the patient; and
an impedance measuring circuit electrically coupled to the at least one catheter electrode, the first return patch electrode, and the second return patch electrode, the impedance measuring circuit configured to:
drive currents between the at least one catheter electrode, the first return patch electrode, and the second return patch electrode, wherein each of the driven currents comprises a unique frequency;

detect, using a voltage at the at least one catheter electrode as a reference voltage, voltages generated in response to the driven currents; and simultaneously measure impedances based on the driven currents and the detected voltages.

2. The tissue therapy system of claim 1, wherein the first return patch electrode is a first portion of a return patch, and wherein the second return patch electrode is a second portion of the return patch.

3. The tissue therapy system of claim 1, wherein the first return patch electrode is a first return patch, and wherein the second return patch electrode is a second return patch.

4. The tissue therapy system of claim 1, wherein the impedance measuring circuit comprises:

a first signal generator configured to drive a first current between the first return patch electrode and the second return patch electrode at a first frequency;

a second signal generator configured to drive a second current between the first return patch electrode and the at least one catheter electrode at a second frequency; and a third signal generator configured to drive a third current between the second return patch electrode and the at least one catheter electrode at a third frequency, wherein the first, second, and third frequencies are different from each other.

5. The tissue therapy system of claim 4, wherein the impedance measuring circuit is configured to simultaneously measure the impedances.

6. The tissue therapy system of claim 1, wherein to measure impedances, the impedance measuring circuit is configured to measure i) a first impedance between the first return patch electrode and the patient and ii) a second impedance between the second return patch electrode and the patient.

7. The tissue therapy system of claim 6, further comprising a processing device coupled to the impedance measuring circuit, the processing device configured to:

compare the first impedance to the second impedance; and generate an alert when the first impedance and the second impedance are substantially different.

8. The tissue therapy system of claim 1, wherein to measure impedances, the impedance measuring circuit is configured to measure i) a first impedance between the first return patch electrode and the at least one catheter electrode and ii) a second impedance between the second return patch electrode and the at least one catheter electrode.

9. The tissue therapy system of claim 1, further comprising a processing device coupled to the impedance measuring circuit, the processing device configured to output impedance data that includes at least one complex impedance including a real (resistive) element and an imaginary (reactive) element.

10. An impedance measuring circuit for use in a tissue therapy system, the impedance measuring circuit electrically coupleable between i) at least one electrode of a catheter insertable in a patient, ii) a first return patch electrode configured to be applied to skin of the patient, and iii) a second return patch electrode configured to be applied to the skin of the patient, the impedance measuring circuit configured to:

drive currents between the at least one catheter electrode, the first return patch electrode, and the second return patch electrode, wherein each of the driven currents comprises a unique frequency;

detect, using a voltage at the at least one catheter electrode as a reference voltage, voltages generated in response to the driven currents; and simultaneously measure impedances based on the driven currents and the detected voltages.

11. The impedance measuring circuit of claim 10, wherein the impedance measuring circuit comprises:

a first signal generator configured to drive a first current between the first return patch electrode and the second return patch electrode at a first frequency;

a second signal generator configured to drive a second current between the first return patch electrode and the at least one catheter electrode at a second frequency; and a third signal generator configured to drive a third current between the second return patch electrode and the at least one catheter electrode at a third frequency, wherein the first, second, and third frequencies are different from each other.

12. The impedance measuring circuit of claim 11, wherein the impedance measuring circuit is configured to simultaneously measure the impedances.

13. The impedance measuring circuit of claim 10, wherein to measure impedances, the impedance measuring circuit is configured to measure i) a first impedance between the first return patch electrode and the patient and ii) a second impedance between the second return patch electrode and the patient.

14. The impedance measuring circuit of claim 10, further comprising:

a first input buffer coupled to the first return patch electrode;

a first RC filter coupled to an input of the first input buffer;

a second input buffer coupled to the second return electrode; and a second RC filter coupled to an input of the second input buffer.

15. The impedance measuring circuit of claim 10, wherein the impedance measuring circuit is configured to be electrically coupled to an ablation pulse generator, and wherein the impedance measuring circuit is protected from ablation pulses generated by the ablation pulse generator.

16. A method of measuring impedances in a tissue therapy system, the method comprising:

driving, using an impedance measuring circuit, currents between i) at least one electrode of a catheter insertered in a patient, ii) a first return patch electrode applied to skin of the patient, and iii) a second return patch electrode applied to the skin of the patient, wherein each of the driven currents comprises a unique frequency;

detecting, by the impedance measuring circuit, using a voltage at the at least one catheter electrode as a reference voltage, voltages generated in response to the driven currents; and simultaneously measuring impedances based on the driven currents and the detected voltages.

17. The method of claim 16, wherein the first return patch electrode is a first portion of a return patch, and wherein the second return patch electrode is a second portion of the return patch.

18. The method of claim 16, wherein the first return patch electrode is a first return patch, and wherein the second return patch electrode is a second return patch.

19. The method of claim 16, wherein driving currents comprises:

driving a first current between the first return patch electrode and the second return patch electrode at a first frequency;

driving a second current between the first return patch electrode and the at least one catheter electrode at a second frequency; and driving a third current between the second return patch electrode and the at least one catheter electrode at a third frequency, wherein the first, second, and third frequencies are different from each other.

\* \* \* \* \*